United States Patent [19]

Georgiev et al.

[11] Patent Number: 4,845,122
[45] Date of Patent: Jul. 4, 1989

[54] ANTI-ALLERGY TREATMENT USING 2-(SUBSTITUTED AMINO)-4,5-DIHYDRO-4-OXO-3-FURAN-CARBOXYLIC ACIDS AND DERIVATIVES THEREOF

[76] Inventors: Vassil S. Georgiev, 3248 Winton Rd. South #K-32, Rochester, N.Y. 14623; Clyde R. Kinsolving, 16 Bent Oak Trail, Fairport, N.Y. 14450; Robert A. Mack, 817 Elmwood Ter., Rochester, N.Y. 14620

[21] Appl. No.: 938,305

[22] Filed: Dec. 5, 1986

[51] Int. Cl.$^4$ ............................................. A61K 31/34
[52] U.S. Cl. .................................... 514/472; 514/826
[58] Field of Search ................................ 514/472, 826

[56] References Cited

PUBLICATIONS

Prabhakar, S.; Pai, B. R.; Ramachandran, V. N. *Indian J. Chem.* 9, 191 (1971).
Govindachari, T. R.; Prabhakar, S.; Ramachandran, V. N.; Pai, B. R. *Indian J. Chem.* 9, 1031 (1971).
Mester, I.; Ionescu, M. *Phytochemistry* 10, 2205, (1971), C.A. 129976a, vol. 75, 312, (1971).
Ramachandran, V. N.; Pai, B. R.; Somasundaram, N.; Swaninathan, C. S. *Indian J. Chem.* 11, 1088 (1973), C.A. 10872a 80, 440, (1974).
Gais, H. J.; Hafner, J. *Heterocycles* 4, 1921, (1976), C.A. 1212676 86, 542 (1977).
Yazima, T.; Munakat, K. *Agic. Biol. Chem.* 44, 235. (1980).
Capuano, L.; Fischer, W. *Chem. Ber., 109, 212, (1976).*
Mulholland, T. P. C.; Foster, R.; Haydock, D. B., *J. Chem. Soc.; Perkin Trans I* 1972; 1225.
Ibrahim, N. S. et al., 2, *Naturforsch., 40B, pp. 129-131, Mar. 1985.*

*Primary Examiner*—Leonard Schenkman

[57] ABSTRACT

As an anti-allergic treatment for warm-blooded animals, therapeutic amounts of a compound having the formula I (including acid salts thereof) or II are administered:

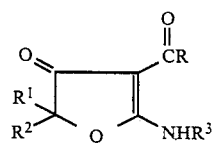

where;
R is $OR^4$ or $NHR^5$ in which $R^4$ is hydrogen or lower alkyl, $R^5$ is selected from phenyl and phenyl monosubstituted with halogen, lower alkyl, lower alkoxy, $R^1$ and $R^2$ are independently hydrogen or lower alkyl, and
$R^3$ is selected from lower alkyl, arylcyclopropyl, naphthyl, phenyl, and phenyl monosubstituted with lower alkyl, lower alkoxy, trifluoromethyl, halogen, nitro, carboxyl, or ethyl carboxylate;

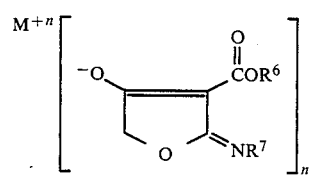

$R^6$ is lower alkyl, $R^7$ is selected from phenyl and phenyl monosubstituted with lower alkyl, lower alkoxy, halogen or acetyl, and M is an alkali or alkaline earth metal.

8 Claims, No Drawings

ANTI-ALLERGY TREATMENT USING 2-(SUBSTITUTED AMINO)-4,5-DIHYDRO-4-OXO-3-FURANCARBOXYLIC ACIDS AND DERIVATIVES THEREOF

BACKGROUND OF THE INVENTION

This invention relates generally to an anti-allergy treatment and more specifically to such treatment using effective amounts of 2-(substituted amino)-4,5-dihydro-4-oxo-3-furancarboxylic acids and derivatives thereof.

A number of 2-(substituted amino)-4,5-dihydro-4-oxo-3-furancarboxylic acids and their esters and amides have been previously prepared (Capuano, L. et al., Chem. Ber., 109, pp 212–217 (1976); Mulholland, T. P. C. et al., J. Chem. Soc., Perkins Trans I, pp 1225–1231); and Ibrahim, N. S. et al., Z. Naturforsch., 40B, pp 129–131, (Mar. 1985). No biological activity for the latter compounds is reported. We have found that these compounds as well as other similarly prepared derivatives are useful as anti-allergic agents.

Hay fever, perennial allergic rhinitis and bronchial asthma all can result from the inhalation of specific antigenic materials in susceptible individuals. The interaction of the allergen with mast cells leads to the release of a variety of vasoactive, chemotactic and enzymatic mediators which are presumed to be responsible for the vasodilation, edema, increased mucous secretion and other symptomatology that are characteristic of these diseases. Administration of the furanone compounds of the invention led to inhibition of the allergic mediator release. Although the mechanism by which the compounds function is not absolutely known, applicants have found that the furanones are active in vivo in the Rat Active Anaphylaxis Model and inhibit mediator release from sensitized rat mast cells. They also inhibit wheal formation and flare reactions produced in rats by the intradermal injection of the allergic mediators histamine, serotonin or bradykinin.

BRIEF SUMMARY OF THE INVENTION

In accordance with this invention there is provided an anti-allergic treatment method which comprises administering to a warm-blooded animal a compound selected from (a) compounds having the formula I, (b) pharmaceutically acceptable acid salts of the compounds of formula I, and (c) compounds having the formula II, in an amount effective to inhibit allergic mediator release. Compounds having formula I are as follows:

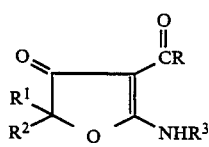

where;

R is $OR^4$ or $NHR^5$ in which $R^4$ is hydrogen or lower alkyl, $R^5$ is selected from phenyl and phenyl monosubstituted with halogen, lower alkyl or lower alkoxy, $R^1$ and $R^2$ are independently hydrogen or lower alkyl, and $R^3$ is selected from lower alkyl, arylcyclopropyl, naphthyl, phenyl, and phenyl monosubstituted with lower alkyl, lower alkoxy, trifluoromethyl, halogen, nitro, carboxyl, or ethyl carboxylate;

Compounds having formula II are as follows:

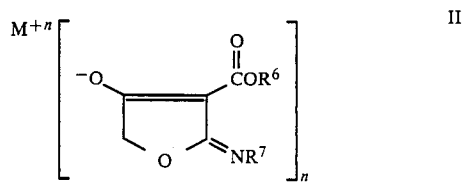

where;

n is 1 or 2 $R^6$ is lower alkyl, $R^7$ is selected from phenyl and phenyl monosubstituted with lower alkyl, lower alkoxy, halogen or acetyl, and M is an alkali or alkaline earth metal.

DETAILED DESCRIPTION

As used herein lower alkyl and lower alkoxy mean straight or branched chain alkylene groups having 1 to 4 carbon atoms and halogen means chlorine, bromine, iodine and fluorine. By arylcyclopropyl is meant the moiety:

Where $R^8$ is phenyl or phenyl substituted with lower alkyl and/or halogen.

The acid esters of formula I above can be prepared by a base-catalyzed cyclocondensation of an alkyl 2-(haloacetyl), 2-(2-halopropionyl) or 2-(2-haloisobutyryl) acetate with an appropriate isocyanate as described, for example, in the previously mentioned article by Capuano et al. The free acids are prepared from the esters by alkaline hydrolysis. Pharmaceutically acceptable salts of the acids can be prepared by treatment of the esters with a weak aqueous base ($Na_2CO_3$ or $K_2CO^3$) and the enol salts of formula II by treatment of the esters with an alcoholic solution of a strong base such as 1 to 2 molar KOH, NaOH, $Mg(OH)_2$ or $Ca(OH)_2$ in ethanol. The acid amides can be prepared by reacting a 4-bromoacetoacetanilide prepared according to the method of Mallams and Israelstam, J. Or. Chem., 29, p 3554 (1968) or Ali et al., J. Chem Eng. Data, 17, p 106 (1972) with an appropriate isocyanate under conditions similar to those described in the previously mentioned article by Ibrahim et al.

Procedure for the Preparation of Ethyl 2-(Substituted amino)-4,5-dihydro-4-oxo-3-furancarboxylates

Preparation of Ethyl 2-[[4-(ethoxycarbonyl)phenyl]amino]4,5-dihydro-4-oxo-3-furancarboxylate Triethylamine (9.87 ml) was added dropwise, over a period of 1 hour to a cooled (ice bath) solution of ethyl 4-chloroacetoacetate (9.87 g, 60 mmol) and ethyl p-isocyanatobenzoate (14.34 g, 75 mmol) in 60 ml of petroleum ether-ethyl acetate (10:1 by volume), under nitrogen atmosphere. The reaction mixture was stirred at 0°–5° C. for 1 hour. The resulting ethyl 2-[[4-(ethoxycarbonyl)phenyl]-amino]-4,5-dihydro-4-oxo-3-furancarboxylate was filtered and then washed sequentially with petroleum ether, 1 N hydrochloric acid and water. Yield 13.0 g Mp 152°–153° C. (isopropanol).

Other ester derivatives are similarly prepared by reacting ethyl 4-chloroacetoacetate with:

(a) methyl isocyanate
(b) isopropyl isocyanate
(c) 2-methoxyphenyl isocyanate
(d) 3-methylphenyl isocyanate
(e) 3-(trifluoromethyl)phenyl isocyanate
(f) 3-nitrophenyl isocyanate
(g) 4-chlorophenyl isocyanate
(h) 4-bromophenyl isocyanate
(i) 1-naphthyl isocyanate
(j) phenyl isocyanate
(k) trans-2-phenylcyclopropyl isocyanate
(l) trans-2-(4-chlorophenyl)cyclopropyl isocyanate
(m) trans-2-(4-methylphenyl)cyclopropyl isocyanate Procedure for the Preparation of 2-(Substituted amino)-4,5-dihydro-4-oxo-3-furancarboxylic Acids Preparation of 2-[(4-Carboxyphenyl)amino]-4,5-dihydro-4-oxo-3-furancarboxylic Acid The acid ester, ethyl 2-[[4-ethoxycarbonyl)phenyl]amino]-4,5-dihydro-4-oxo-3-furancarboxylate was suspended in 8% by weight aqueous sodium carbonate solution and stirred. Using a glass, subsurface delivery tube, steam was passed through the mixture for 0.5 to 1.5 hours (preferably 0.5 hour). The resulting solution was cooled to 20° C., filtered and the filtrate acidified to pH 1 by the gradual addition of concentrated hydrochloric acid at 0°–5° C. (ice water bath). The precipitated free acid was filtered off, rinsed with water and dried on the filter. Recrystallization from aqueous ethanol provided the free acid in 55–60% of theoretical yield.

Other free acid derivatives in this series are obtained by the same procedure. Besides steam passage for from about 0.5 to 1.5 hours, some derivatives require additional heating at reflux for from about 1–3 hours to complete the reaction. The yields obtained are usually 60–70% of theory.

During the hydrolysis of two esters, the ethyl 4,5-dihydro-5-methyl-4-oxo-2-(phenylamino)-3-furancarboxylate and the ethyl 4,5-dihydro-5,5-dimethyl-4-oxo-2-(phenylamino)-3-furancarboxylate, the corresponding decarboxylated derivatives were isolated as by-products, namely, (a) 2-methyl-5-(phenylamino)-3(2H)-furanone, m.p. 191°–193° C. (ethyl acetate). Anal. Calcd. $C_{11}H_{11}NO_2$: C, 69.83; H, 5.86; N, 7.40. Found: C, 69.76; H, 5.92; N, 7.35.

(b) 2,2-dimethyl-5-(phenylamino)-3(2H)-furanone, m.p. 200°–202° C. (toluene). Anal. Calcd. for $C_{12}H_{13}NO_2$: C, 70.92; H, 6.45; N, 6.89. Found: C, 70.86; H, 6.45; N, 6.81.

Procedure for the Preparation of Acid Salts 4,5-Dihydro-4-oxo-2-(phenylamino)-3-furancarboxylic acid ethyl ester (10.13 g, 41 mmol) was added in one portion to a solution of sodium carbonate monohydrate (9.92 g, 80 mmol) in 100 ml water. Steam was then passed through the mixture until the ester completely dissolved (1–2 hours). The reaction mixture was filtered while still hot. Cooling of the filtrate (ice/water bath) provided the crystalline sodium salt. Recrystallization from a minimum amount of distilled water gave 4.53 g of the pure product, 4,5-dihydro-4-oxo-2-phenylamino-3-furancarboxylic acid sodium salt, m.p. <300° C.

Other acid salts are prepared by treating the respective acid esters according to the above procedure.

Procedure for the Preparation of Enol Salts

Preparation of Potassium 2,5-dihydro-3-ethoxycarbonyl-2-(phenylimino)-4-furanyloxide Under nitrogen atmosphere, a solution of potassium hydroxide (5.33 g, 81 mmol) in 50 ml ethanol was added dropwise (over a period 75 min) to a stirred solution of 4,5-dihydro-4-oxo-2-(phenylamino)-3-furancarboxylic acid ethyl ester (20 g, 81 mmol) in 450 ml ethanol while cooling (ice/water bath). The reaction mixture was stirred at room temperature for 30 min and then refluxed for another 30 min. The solid precipitate was filtered off while still hot, then rinsed repeatedly with ethanol, followed by ether. After drying, 20.10 g of the white crystalline salt, potassium 2,5-dihydro-3-ethoxycarbonyl-2-(phenylimino)-4-furanyloxide, were obtained, m.p <300° C.

Other enol salts are prepared by treating the respective acid esters according to the above procedure.

Procedure of the Preparation of 4,5-Dihydro-4-oxo-N-(phenyl or substituted phenyl)-2-(substituted amino)-3-furancarboxamides Preparation of 4,5-dihydro-4-oxo-N-phenyl-2-(phenylamino)-3-furancarboxamide 4-Bromoacetoacetanilide Under a nitrogen atmosphere, a solution of bromine (1.16 ml, 22.59 mmol) in 17 ml of acetic acid containing a small crystal of iodine was added over 2.5 hours to a solution of acetoacetanilide (4.0 g, 22.57 mmol) in 12 ml of acetic acid, at room temperature (cooling with cold water). The reaction mixture was stirred at room temperature for 3 hours, then poured into 100 ml of ice-cold water and the crude solid product was filtered off. Following crystallization from ethanol, 3.30 g of 4-bromoacetoacetanilide were obtained, m.p 130°–132° C.

4,5-Dihydro-4-oxo-N-phenyl-2-(phenylamino)-3-furancarboxamide

Under a nitrogen atmosphere, sodium hydride (97%; 0.633 g, 25.61 mmol) was weighed into a dry reaction vessel and covered with 55 ml of anhydrous dioxane. A solution of phenyl isocyanate (1.39 ml, 12.81 mmol) in 5 ml of anhydrous dioxane was then added over a 5-10 minute period at room temperature (cooling with cold water). Next, the 4-bromoacetoacetanilide (3.28 g, 12.8 mmol) was added portionwise over a 20-minute period. The reaction mixture was stirred at 20°–25° C. for 5 hours, filtered under nitrogen atmosphere, and poured into 300 ml of ice-cold water. After acidifying (pH 5-6) with several drops of concentrated hydrochloric acid, the crude product was filtered off and crystallized from ethanol to provide 2.8 g. of amide product, m.p. 182°-184° C.

Other amide derivatives are prepared by a similar procedure.

For pharmaceutical purposes, the compounds can be administered to warm-blooded animals perorally, parenterally or intranasally as active ingredients in customary dosage unit compositions. These dosage unit compositions contain the active ingredient and at least one inert pharmaceutical carrier. Dosage unit forms contemplated by the present invention include tablets, capsules, solutions, suspensions, aerosols, and parenteral compositions such as intramuscular, intravenous or intradermal preparations. Sustained release dosage forms are also contemplated where the active ingredient is bound to an ion exchange resin which, optionally, can be coated with a diffusion barrier coating to modify the release properties of the resin.

The quantity of active ingredient administered in such dosage forms can vary over a wide range depending upon the mode of administration, the size and weight of the patient and whether the nature of the treatment is prophylactic or therapeutic in nature. In general, dosage unit forms contain from about 5 mg to 250 mg of the active ingredient and in man the dosage is administered from 1 to 4 times daily. The total daily dosage will be from about 5 mg to 1000 mg although lower or higher amounts can be used. A preferred total daily dosage would be from 10 mg to 100 mg of active ingredient.

Pharmaceutical carriers or excipients used in the preparation of pharmaceutical compositions for use in the invention may be either organic or inorganic, solid or liquid in nature. Suitable solid excipients include gelatin, microcrystalline cellulose, lactose, starches, and magnesium stearate. Suitable liquid excipients include water and alcohols such as ethanol, benzyl alcohol and polyethylene glycols. The preferred liquid excipients for injectable preparations include water, saline solution, dextrose solution and glycol solutions such as aqueous propylene glycol or aqueous polyethylene glycol. The properties of the formulations may be enhanced by the addition of one or more adjuvants possessing properties as viscosity enhancers, surfactants, pH modifiers, preservatives, sweeteners, stability enhancers, coloring agents, suspending agents, granulating agents, coating agents, disintegration modifiers, propellants, emulsifying agents and humectants.

EXAMPLE 1

The furanone compounds listed in Tables 1A, 1B and 2 were used for anti-allergy treatment in the rat active anaphylaxis model and/or the rat dermal vascular permeability test (mediator release model). Peroral administration was used in the permeability test except as indicated in the Tables. The results are given as the percent inhibition from the control.

In the rat active anaphylaxis model, groups consisting of 15-20 male rats are intraperitoneally sensitized on day zero with 500 ug of bovine serum albumin-absorbed alum admixed with $2 \times 10^{10}$ killed Bordatella pertussis vaccine organisms. Fourteen days later, the right hind paw is injected subcutaneously with 100 ug of bovine serum albumin one hour post compound administration at a dosage of 100 mg/kg of rat weight intraperitoneally as a 0.85% solution in saline. The paw volume is measured using a mercury plethysmometer prior to drug administration and 90 minutes post antigenic challenge. The percent inhibition of edema is calculated as the difference in volume between the control and drug treated groups divided by the control volume times 100. The positive control drug, theophylline (90 mg/kg, po) is included in each assay. Statistical analysis of the data is done using the poolt program.

In the rat dermal vascular permeability test, groups of ten male rats are intraperitoneally or perorally administered either the test compound, at a dosage of 100 mg/kg of rat weight as a 0.85% solution in saline, or the positive reference standard cyproheptadine (1 mg/kg) one hour prior to an intravenous injection of 1 ml of a 0.5% solution of Evan's blue dye into naive animals. Ten minutes later the animals are challenged by intradermally injecting 0.1 ml of a solution of either serotonin (1 ug/ml), histamine (20 ug/ml) or bradykinin (10 ug/ml) into separate sites on the back. Five minutes following challenge the animals are killed, the skin retracted, and the mean diameter of the blue wheal and flare reactions are determined. The percent inhibition of the wheal reaction is calculated as the difference in diameter between the saline control and drug treated groups divided by the control diameter times 100. Statistical analysis of the data is done using the poolt program.

TABLE 1A

| Compound I | | | | Active Anaphylaxis | % Inhibition of Mediator Release | | | | Recrys. |
|---|---|---|---|---|---|---|---|---|---|
| R | $R^1$ | $R^2$ | $R^3$ | % Inhibition | Serotonin | Histamine | Bradykinin | mp °C. | Solvent |
| $OC_2H_5$ | H | H | $CH_3$ | — | 38 [2] | 50[2] | 25[2] | 179-181 | i-PrOH |
| OH | H | H | $C_6H_5$ | 81,69 | — | — | — | 159-616 | Toluene |
| OH | H | H | $C_6H_4OCH_3$—2 | 45 | 30 | 27 | 38 | 161-164 | i-PrOH |
| $OC_2H_5$ | H | H | $C_6H_4CF_3$—3 | — | 9.7 | 4.1 | 40 | 167-170 | i-PrOH |
| OH | H | H | $C_6H_4NO_2$—3 | 39[1] | 18 | 16 | 48 | 215-218 | THF/$H_2O$ |
| $OC_2H_5$ | H | H | $C_6H_4Cl$—4 | — | 6.6 | 3.3 | 9.5 | 179-181 | i-PrOH |
| OH | H | H | $C_6H_4Br$—4 | 27 | 39 | 45 | 68 | 195-197 | Xylene |
| OH | H | H | $C_6H_4CF_3$—3 | 45 | 40 | 26 | 54 | 170-173 | Toluene |
| OH | H | H | $C_6H_4CO_2H$—4 | 52 | 63 | 64 | 64 | 222(dec.) | EtOH/$H_2O$ |
| $OC_2H_5$ | H | H | $C_6H_4CO_2C_2H_5$—4 | — | 18 | 21 | 21 | 152-153 | i-PrOH |
| OH | H | H | | 64 | — | — | — | 160-161 | i-PrOH |
| $OC_2H_5$ | H | $CH_3$ | $C_6H_5$ | 20,61 | — | — | — | 93-95 | c-Hexane |
| OH | H | $CH_3$ | $C_6H_5$ | 60 | 37[2] | 40[2] | 46[2] | 118-121 | c-Hexane |

[1]edema increased
[2]intraperitoneal administration

TABLE 1B

| Compound I | | | | Active Anaphylaxis | % Inhibition of Mediator Release | | | | Recrys. |
|---|---|---|---|---|---|---|---|---|---|
| R | R¹ | R² | R³ | % Inhibition | Serotonin | Histamine | Bradydinin | mp °C. | Solvent |
| $OC_2H_5$ | $CH_3$ | $CH_3$ | $C_6H_5$ | 16 | — | — | — | 101–103 | c-Hexane |
| OH | $CH_3$ | $CH_3$ | $C_6H_5$ | 44 | — | — | — | 129–131 | c-Hexane |
| $O^-Na^+$ | H | H | $C_6H_5$ | 17 | — | — | — | decomp. | $H_2O$ |
| $NHC_6H_5$ | H | H | $C_6H_5$ | 46 | — | — | — | 182–184 | EtOH |
| $NHC_6H_4Cl-4$ | H | H | $C_6H_4Cl-4$ | — | 14 | 15 | 44 | 241–243 | Dioxane |
| $NH_6H_4OCH_3-4$ | H | H | $C_6H_4OCH_3-4$ | — | 13 | 8 | 39 | 202–204 | THF |
| $NHC_6H_4OCH_3-2$ | H | H | $C_6H_4OCH_3-2$ | — | 18 | 1 | 39 | 172–174 | EtOH |
| $NHC_6H_4CH_3-2$ | H | H | $C_6H_4CH_3-2$ | — | 9 | 0 | 7 | 188–190 | 95% EtOH |
| $OC_2H_5$ | H | H | △—$C_6H_5$ | — | 57 | 35 | 59 | 140–142 | i-PrOH |
| $OC_2H_5$ | H | H | △—$C_6H_4Cl-4$ | — | 51 | 60 | 76 | 146–148 | i-PrOH |
| OH | H | H | △—$C_6H_4CH_3-4$ | 45 | 100 | 100 | 100 | 155–157 | EtOH |
| OH | H | H | △—$C_6H_4Cl-4$ | 6 | 54 | 56 | 71 | 173–175 | EtOH |
| ONa | H | H | △—$C_6H_5$ | 22 | — | — | — | decomp. | $H_2O$ |

TABLE 2

| Compound II[2] | | | Active Anaphylaxis % | % Inhibition of Mediator Release[1] | | |
|---|---|---|---|---|---|---|
| M | R⁷ | R⁶ | Inhibition | Serotonin | Histamine | Bradykinin |
| K | $C_6H_5$ | $C_2H_5$ | 49 | 42 | 31 | 51 |
| K | $C_6H_4CH_3-3$ | $C_2H_5$ | — | 75 | 71 | 70 |
| K | $C_6H_4COCH_3-4$ | $C_2H_5$ | 56 | 79 | 88 | 86 |
| K | $C_6H_4NO_2-3$ | $C_2H_5$ | 37 | 45 | 49 | 67 |
| K | $C_6H_4OCH_3-2$ | $C_2H_5$ | 58 | — | — | — |
| K | $C_6H_4Br-4$ | $C_2H_5$ | 38 | 46 | 65 | 69 |

[1]intraperitoneal administration
[2]Salts all decompose at >300° C.

We claim:

1. An anti-allergic treatment method comprising administering to a warm-blooded animal an effective amount of a compound selected from (a) compounds having formula I, (b) pharmaceutically acceptable acid salts of the compounds of formula I, and (c) compounds having formula II:

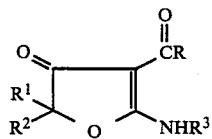

where;
R is $OR^4$ or $NHR^5$ in which $R^4$ is hydrogen or lower alkyl, $R^5$ is selected from phenyl and phenyl monosubstituted with halogen, lower alkyl, lower alkoxy, $R^1$ and $R^2$ are independently hydrogen or lower alkyl, and $R^3$ is selected from lower alkyl, arylcyclopropyl, napthyl, phenyl, and phenyl monosubstituted with lower alkyl, lower alkoxy, trifluoromethyl, halogen, nitro, carboxyl, or ethyl carboxylate;

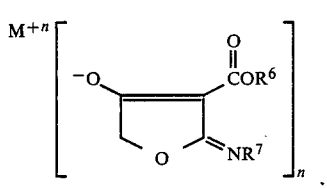

where;
n is 1 or 2, $R^6$ is lower alkyl, $R^7$ is selected from phenyl and phenyl monosubstituted with lower alkyl, lower alkyl, lower alkoxy, halogen or acetyl, and M is an alkali or alkaline earth metal.

2. The method of claim 1 wherein the compound has the formula I.

3. The method of claim 1 wherein the compound has the formula II.

4. The method of claim 2 wherein R is $OR^4$.

5. The method of claim 2 wherein R is $NHR^5$.

6. The method of claim 2 wherein the compound is an acid salt.

7. The method of claim 2 wherein R is $OR^4$ and $R^3$ is arylcyclopropyl.

8. The method of claim 1 wherein the compound is administered perorally, parenterally or intranasally in a dosage unit form containing from about 5 mg to 250 mg of compound and at least one inert pharmaceutical carrier in daily amounts of compound of from about 5 mg to 1000 mg.

* * * * *